United States Patent [19]
Horan et al.

[11] Patent Number: 5,206,143
[45] Date of Patent: Apr. 27, 1993

[54] METHOD AND REAGENTS FOR PERFORMING SUBSET ANALYSIS USING QUANTITATIVE DIFFERENCES IN FLUORESCENCE INTENSITY

[75] Inventors: Paul K. Horan, West Chester; Sue E. Slezak, Downingtown, both of Pa.

[73] Assignee: SmithKline Beecham Corporation, King of Prussia, Pa.

[21] Appl. No.: 818,473

[22] Filed: Jan. 6, 1992

Related U.S. Application Data

[63] Continuation of Ser. No. 296,394, Jan. 9, 1989, abandoned, which is a continuation of Ser. No. 794,945, Nov. 1, 1985, abandoned.

[51] Int. Cl.$^5$ .................. C07K 15/28; C12Q 1/00; C01N 15/10; C01N 33/533
[52] U.S. Cl. .................. 435/7.24; 435/810; 436/537; 436/546; 436/166; 436/172; 530/391.3
[58] Field of Search ............... 435/7.2, 7.24, 29, 808, 435/810, 973, 7.23, 975, 7.94; 436/536, 546, 56, 528, 172, 805, 537, 52, 166, 826; 530/391.3

[56] References Cited

U.S. PATENT DOCUMENTS

| | | | |
|---|---|---|---|
| 3,883,247 | 5/1975 | Adams | 356/39 |
| 4,284,412 | 8/1981 | Hansen et al. | 23/230 |
| 4,378,344 | 3/1983 | Zahradnik et al. | 436/500 |
| 4,475,236 | 10/1984 | Hoffman | 382/6 |
| 4,499,052 | 2/1985 | Fulwyler | 422/52 |
| 4,520,110 | 5/1985 | Stryer et al. | 436/501 |
| 4,550,017 | 10/1985 | Liu et al. | 424/11 |
| 4,607,007 | 8/1986 | Lanier et al. | 436/548 |

FOREIGN PATENT DOCUMENTS

| | | |
|---|---|---|
| 1248873 | 1/1989 | Canada. |
| 0022670 | 1/1981 | European Pat. Off.. |
| 0076695 | 4/1983 | European Pat. Off.. |
| 0121262 | 10/1984 | European Pat. Off.. |
| 0126450 | 11/1984 | European Pat. Off.. |

OTHER PUBLICATIONS

"Phosphamethine cyanine dyes with benzimidazolyl substituents", Dimroth et al., *Chemical Abstracts*, No. 44709f, vol. 83, No. 6, Aug. 11, 1975, p. 69.

"Immunoassay Techniques with Fluorescent Phycobiliprotein Conjugates", Kronick et al., *Clinical Chemistry*, vol. 29, No. 9, pp. 1592-1586, Sep. 1983.

"Flow Cytometry: Present and Future", Muirhead et al., *Biotechnology*, vol. 3, Apr. 1985.

Shapiro, H. M., *Practical Flow Cytometry*, pp. 119-128 (1985).

Loken, M. R., and Linier, L. L., *Three Color Immunofluorescence Analysis of Leu Antigens on Human Peripheral Blood Using Two Lasers on a Fluorescence-Activated Cell Sorter*, Cytometry, 5:151-158 (1984).

Oi, V. T., et al., *Fluorescent Phycobiliprotein Conjugates for Analyses of Cells and Molecules*, J. Cel. Biol. 93:981-86 (1982).

*Primary Examiner*—Esther L. Kepplinger
*Assistant Examiner*—Nancy Parsons
*Attorney, Agent, or Firm*—Finnegan, Henderson, Farabow, Garrett & Dunner

[57] ABSTRACT

Methods for distinguishing multiple subpopulations of biological particles in a single sample based upon quantitative differences in the fluorescence intensity attributable to one or two fluorochromes with which the biological particles are labelled. The method is used with flow cytometric particle counting techniques to count and sort and biological particles such as the formed elements of blood and other tissue cells. Also disclosed are reagents containing fluorochrome-conjugated antibodies used in the methods.

42 Claims, 5 Drawing Sheets

ANTI-HUMAN LEU-2A/SUPPRESSOR T-LYMPHOCYTES

METHOD AND REAGENTS FOR PERFORMING SUBSET ANALYSIS USING QUANTITATIVE DIFFERENCES IN FLUORESCENCE INTENSITY

This application is a continuation of application Ser. No. 07/296,394 filed Jan. 9, 1989, now abandoned, which is a continuation of application Ser. No. 06/794,945 filed Nov. 1, 1985 now abandoned.

BACKGROUND OF THE INVENTION

1. Field of the Invention

The present invention relates to a method and composition of matter for using quantitative measurements of fluorescence intensity to measure multiple subpopulations of particles from a single sample of particles by flow cytometric techniques.

2. Description of Related Art

Flow cytometry is a rapid, high precision technique for analysis and sorting of many different particles, including formed elements of blood and other biologic tissue cells. Using flow cytometry, particles can be counted and sorted by passing a fluid stream containing the particles through a light beam produced by a laser light source. The particles passing through the light beam scatter the illuminating light; measuring the intensity of scattered light at different angles provides information about the size, shape, density, and surface morphology of the particles. Fluorochrome-labelling of the particles to be analyzed provides an often used alternative to relying on differential refraction of light to analyze the particles. When fluorochrome-labelled particles are counted or sorted, the presence or absence of fluorescence within a selected wavelength range emitted by the labelled particles following excitation by the illuminating light is the parameter measured in making the analysis. Fluorochrome labelling has advantages especially when counting particles of biological origin, because, in comparison to methods relying on measuring light refraction, quantitation of specific biochemicals is possible.

For a great many applications, subset analysis, defined as distinguishing multiple subpopulations of particles in a single sample of particles, would afford great savings in time and expense. Commonly available flow cytometers, which include only one laser and two fluorescence detection channels, used in conjunction with conventional methods, however, are limited to measurement of not more than two fluorescent dyes, and thus, can distinguish no more than two subpopulations of particles in any one sample. Most efforts to enhance the number of subpopulations that can be distinguished in a single sample have relied on using highly sophisticated instruments. Such instruments contain two or more excitation lasers and a sufficient number of fluorescence detection channels to detect fluorescence from three or more fluorochromes. Even using these sophisticated instruments, the number of subpopulations which can be distinguished in a single sample is limited by the finite number of available fluorochromes. Additionally, widespread use of these sophisticated instruments, particularly for routine clinical diagnosis, is restricted by their prohibitively high cost.

Evidence that the need for a method of subset analysis using widely available instruments remains unfulfilled is provided by continuing efforts to develop such a method. In U.S. Pat. No. 4,499,052 to Fulwyler, a method of distinguishing multiple subpopulations of cells from a single sample of cells is described. This method employs several cell-specific antibodies having one hundred percent of the antibody molecules labelled with different, preselected ratios of fluorescein and rhodamine. After reaction with a reagent containing the labelled antibodies, the cells are distinguished and counted by comparing the measured fluorochrome ratios to the preselected fluorochrome ratios and summing the number of cells having each fluorochrome ratio.

Another method for using widely available instruments and fluorochrome-labelled antibodies for subset analysis that permits analysis of a limited number of subpopulations from a single sample recently has been described. Shapiro, H. M., *Practical Flow Cytometry*, 127–128 (1985). According to this method, a sample containing several different cell types is mixed with a reagent containing three different antibodies having each antibody molecule labelled with one fluorochrome. Antibodies specific to one cell type are labelled with fluorochrome A, antibodies specific to a second cell type are labelled with fluorochrome B, and antibodies specific to a third cell type are labelled with the fluorochromes A and B such that approximately one-half the third cell type-specific antibody molecules are labelled with fluorochrome A and the remaining third cell type-specific antibodies are labelled with fluorochrome B. All of the third cell type-specific antibodies have the same antigenic affinity, and thus the maximal measured intensity of each fluorochrome on the third cell type is less than the maximal measured intensity when antibodies having the same antigen affinity conjugated to one fluorochrome are used alone. After reaction with the reagent containing fluorochromes A and B, the subsets, upon passing through the excitation laser, emit light of different colors. For example, if fluorochrome A is red and fluorochrome B is green, the first cell type will emit only red light, the second only green light, and the third will emit red and green light. Thus, the three cell types are counted and separated by segregating red from green from red and green.

The procedures described in the above references have in common the use of fluorochrome-labelled antibodies having one hundred percent of the antibody molecules labelled with fluorochrome. Since precision dictates that the cells to be counted be labelled under antibody excess, cell separation has been restricted to qualitative distinctions between fluorochrome-labelled cells, that is, a cell either does or does not emit a certain color or either does or does not emit a ratio of colors equivalent to a preselected ratio of colors. Absent from the above references is a method of distinguishing subsets based upon quantitative measurements of fluorescence intensity.

SUMMARY OF THE INVENTION

The invention resides in the discovery of a method for using quantitative measurements of fluorescence intensity to perform subset analysis. The invented method makes possible measurement of more than one subset of particles from a single sample using a single fluorochrome. Additionally, using the invented method with two fluorochromes further increases the number of subsets that are measurable from a single sample.

According to the invented method, each subset to be measured is labelled with a different amount of a selected fluorochrome. Then, using flow cytometric techniques, the number of particles in each subset is determined by summing the number of particles exhibiting fluorescence intensities within each measured range between 0% and up to and including 100% intensity (defined as the maximum fluorescence intensity measurable by the instrument and instrument settings used). In addition to determining the number of particles in each subset, the particles may be separated, using standard cell sorting techniques, based upon measured fluorescence intensity.

In a further aspect of the invention, two fluorochromes are employed in performing subset analysis. Each subset to be measured is labelled with one or both fluorochromes so that the amount of each fluorochrome on the particles of any one subset is between 0% and up to and including 100% maximal labelling (defined as the fluorochrome amount that produces 100% fluorescence intensity). The particle subsets then are counted or sorted based upon quantitative measurements of the fluorescence intensity of each fluorochrome exhibited by the particles.

The invention further includes reagents designed for use in the invented method.

DETAILED DESCRIPTION OF THE INVENTION

The present invention is a method for using quantitative measurements of fluorescence intensity to measure multiple subpopulations of particles from a single sample of particles (subset analysis). According to the invented method, using only one fluorochrome, at least two fluorochrome-labelled subsets of particles from one sample may be counted or sorted; using two fluorochromes, from two to five or more fluorochrome-labelled subsets may be analyzed.

Figure 1:
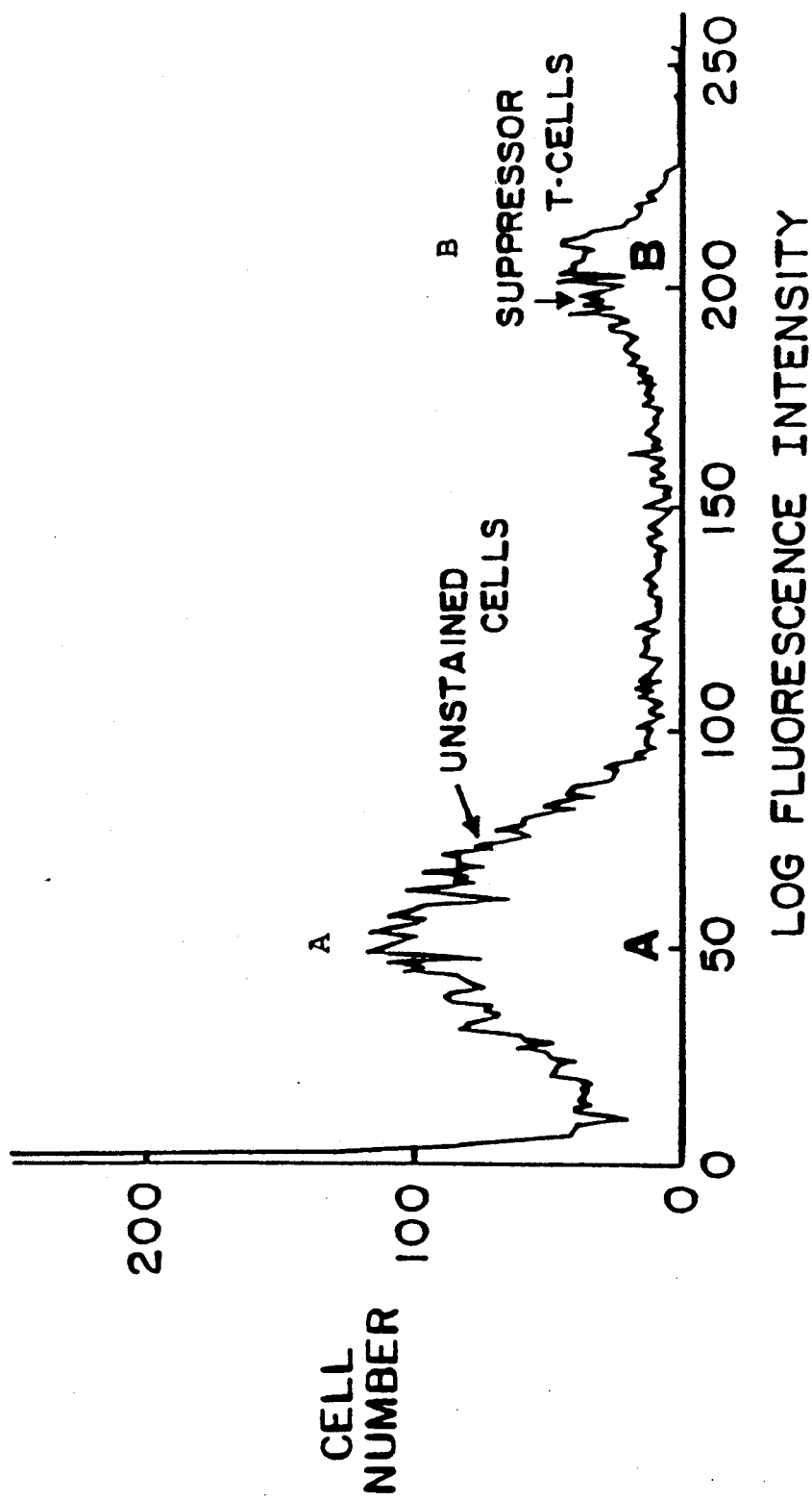
FIG. 1 is a graphic display of the fluorescence distribution obtained by staining a sample of lymphocytes with undiluted phycoerythrin-conjugated human suppressor T-cell antibody.
Figure 2:
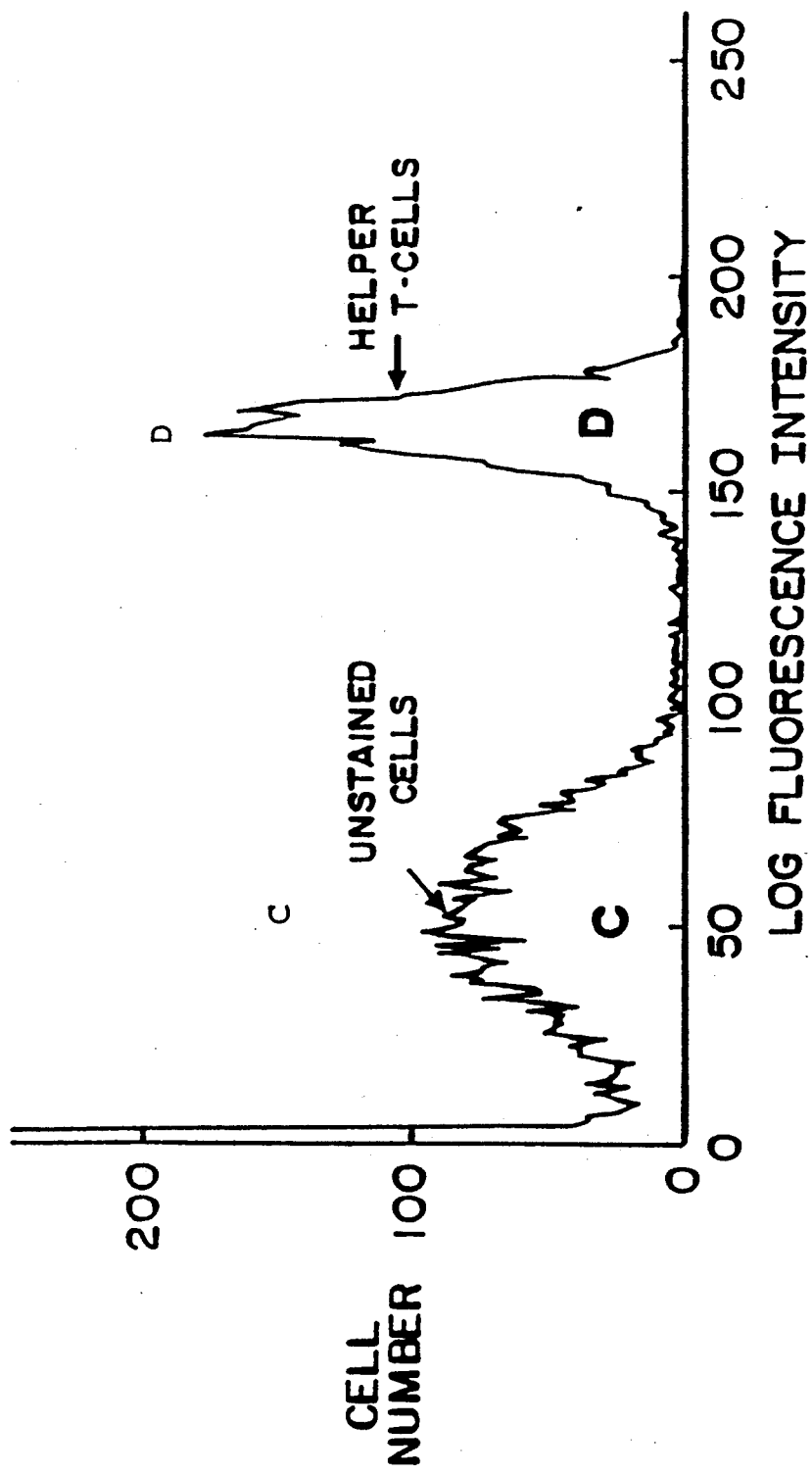
FIG. 2 is a graphic display of the fluorescence distribution obtained by staining a sample of lymphocytes with undiluted phycoerythrin-conjugated human helper T-cell antibodies.

One technique for using flow cytometry to count particles requires that the particles first be fluorochrome-labelled. According to prior art methods, all of the particles in a sample that are stained with a certain fluorochrome are stained to a similar degree which is the amount of fluorochrome that renders the fluorescence intensity of the particles at or near the maximal fluorescence intensity measurable by the instrument employed. The sample, including the stained particles, then is passed through a flow cytometer which counts stained and unstained particles and generates a histogram having fluorescence intensity and cell number as its axes. FIGS. 1 and 2 are exemplary of the histograms that are generated when the particles being counted are cells. As can be seen in FIG. 1, for example, a large number of cells, represented by the peak (A) near the ordinate, essentially are devoid of fluorescence dye and a smaller number of cells, represented by the peak (B) very near the farthest extreme of the fluorescence intensity scale, are stained intensely with fluorochrome. Similarly, in FIG. 2, the unstained cells are located at the peak (C) near the ordinate and the stained cells are at the peak (D) near the far end of the fluorescence intensity scale. FIGS. 1 and 2 thus demonstrate prior art methods of analyzing cells based upon qualitative differences in fluorescence intensity.

In contrast to the above methods that rely on qualitative determinations of fluorescence, the invented method employs quantitative measurements of fluorescence intensity to analyze particles. The initial step in the invented method of counting or sorting multiple subsets of particles from a single sample of particles is to label the particles from each subset with an amount of fluorochrome that differs from the amount applied to the particles from other subsets. Then, preferably using a flow cytometer, the fluorescence intensity exhibited by each particle is measured and the total number of particles having each of the fluorescence intensity levels selected by labelling each of the subsets with a different amount of fluorochrome is determined and the cells are sorted based upon quantitative differences in measured fluorescence intensity.

In its least complicated variation, the invented method is employed to distinguish two subsets using one fluorochrome. Within the population of particles to be analyzed, one subset is labelled with a larger amount of fluorochrome, preferably near the fluorochrome amount that renders the fluorescence intensity of the subset at or near the maximum fluorescence intensity measurable by the instrument and instrument settings being utilized (saturation-labelled), and the other subset is labelled with a smaller amount of fluorochrome, preferably, when analyzing two subsets, the fluorochrome amount that renders the fluorescence intensity of this subset from one-half to two-thirds that of the first subset. Once labelling is complete, the particles are passed through a flow cytometer for counting and separating based upon quantitative differences in fluorescence intensity.

Figure 3:
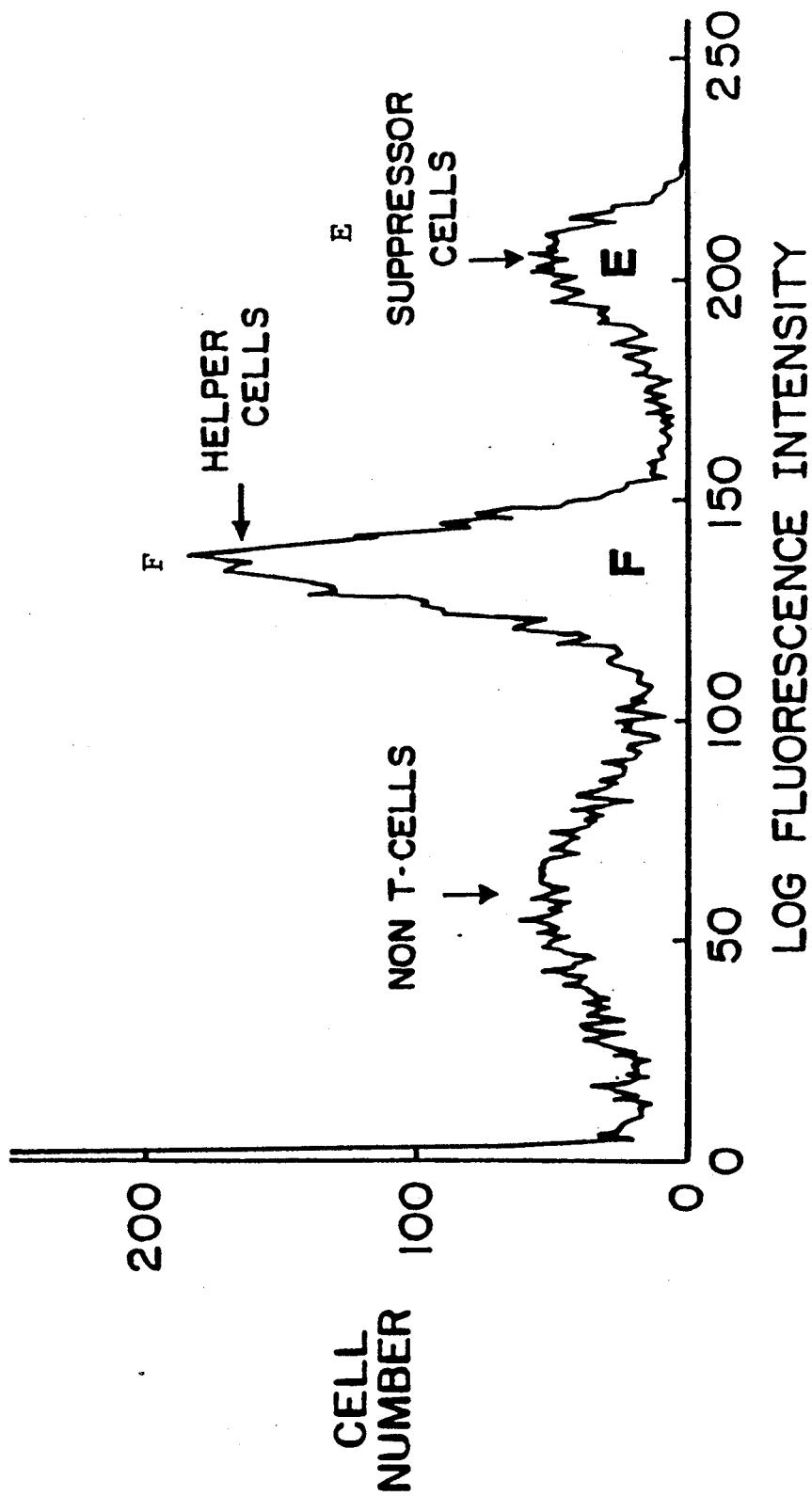
FIG. 3 is a graphic display of the fluorescence distribution obtained by staining a sample of lymphocytes with undiluted phycoerythrin-conjugated antibody to human suppressor T-cells and phycoerythrin-conjugated antibodies to human helper T-cells diluted with unconjugated antibodies to human helper T-cells.

FIG. 3 is an example of a histogram that is generated by flow cytometric counting of two subsets of lymphocytes using the invented method with a single fluorochrome. The saturation-labelled cells are represented by the peak (E) near the far end of the fluorescence intensity axis. The cells stained with a lesser amount of fluorochrome are represented by the peak (F) approximately mid-way along the fluorescence intensity axis. The areas under peaks (E) and (F) provide measurements of the number of cells within each subset.

To analyze a greater number of subsets according to the invented method using one fluorochrome, a greater number of distinguishable fluorochrome label amounts are chosen and affixed to the subsets to be counted. When three subsets are to be counted, preferably the particles are one-third saturation labelled, two-thirds saturation labelled, and saturation labelled. To count four subsets of particles with one fluorochrome, preferably the subsets are one-fourth saturation labelled, one-half saturation labelled, three-fourths saturation labelled, and saturation labelled. Similarly, numbers of subsets in excess of four are analyzed by progressively increasing the number of distinguishable fluorochrome label amounts employed (as defined below).

According to the invented method, differences in fluorescence intensity is the parameter measured to perform subset analysis. Thus, subset analysis requires that the fluorescence intensities of each of the subsets be sufficiently different to be distinguishable by the instrument and instrument settings utilized to make the measurements. As can be seen by reference to FIG. 3, as increasing numbers of different fluorochrome-labelling amounts are employed, the distance between a peak representing one subset and the next closest peak decreases. Once the fluorescence intensities of the subsets becomes so similar that the peaks overlap substantially, the efficiency and reliability of the subset analysis is compromised. Therefore, using the invented method and one fluorochrome, the number of different amounts of fluorochrome label that can be used and thus the number of subsets that can be analyzed is limited to the number that can be labelled with different fluorochrome amounts without causing substantial overlap in the measured fluorescence intensities for each of the subsets.

The number of subsets that can be labelled with different fluorochrome amounts without causing substantial overlap in measured fluorochrome intensity increases in direct proportion to increases in the dynamic range of the log amplifier included in the flow cytometer or other instrument being utilized. Routinely available flow cytometers are outfitted with amplifiers having a three log dynamic range; however, amplifiers having a dynamic range of at least six logs are available and in widespread use for other applications. When an instrument having a six-log dynamic range, for example, is used, the maximum fluorescence intensity detectable by the instrument is greater than the maximum fluorescence intensity detectable by a three-log instrument. Thus, the saturation-staining fluorochrome amount is greater and a larger number of distinguishable fluorochrome-labelling amounts are available for labelling subsets to be analyzed.

The number of subsets that can be labelled with different fluorochrome amounts without causing substantial overlap in measured fluorochrome intensities, also is a function of the uniformity with which the particles of the subsets are fluorochrome-labelled. Thus, a greater number of subsets of synthetic particles, which can be labelled more uniformly (low coefficient of variation), are distinguishable using the invented method than the number of subsets of biological particles, such as tissue cells, which are fluorochrome-labelled more heterogenously (high coefficient of variation). As defined herein, distinguishable subsets means subsets fluorochrome-labelled so that the quantitatively measured fluorescence intensities attributable to the fluorochrome with which they are labelled or at least one of the fluorochromes if they are labelled with more than one fluorochrome do not overlap substantially. Distinguishable fluorochrome amount means an amount of fluorochrome label affixed to the particles of a subset of particles that renders the subset distinguishable from fluorochrome-labelled particles of other subsets based upon quantitative differences in fluorescence intensity of the fluorochrome with which the particles are labelled or at least one of the fluorochromes if the particles are labelled with more than one fluorochrome.

Using the invented method with two fluorochromes further enhances the number of subsets that can be analyzed from a single sample. When utilizing one fluorochrome, the subsets are separated in one dimension, i.e., fluorescence intensity of one fluorochrome. A second fluorochrome makes available another dimension for use in separating the subsets. Using two fluorochromes, the subsets are labelled with distinguishable amounts of one or both fluorochromes and separated based upon quantitative measurements of the fluorescence intensity of each of the fluorochromes.

Figure 4:
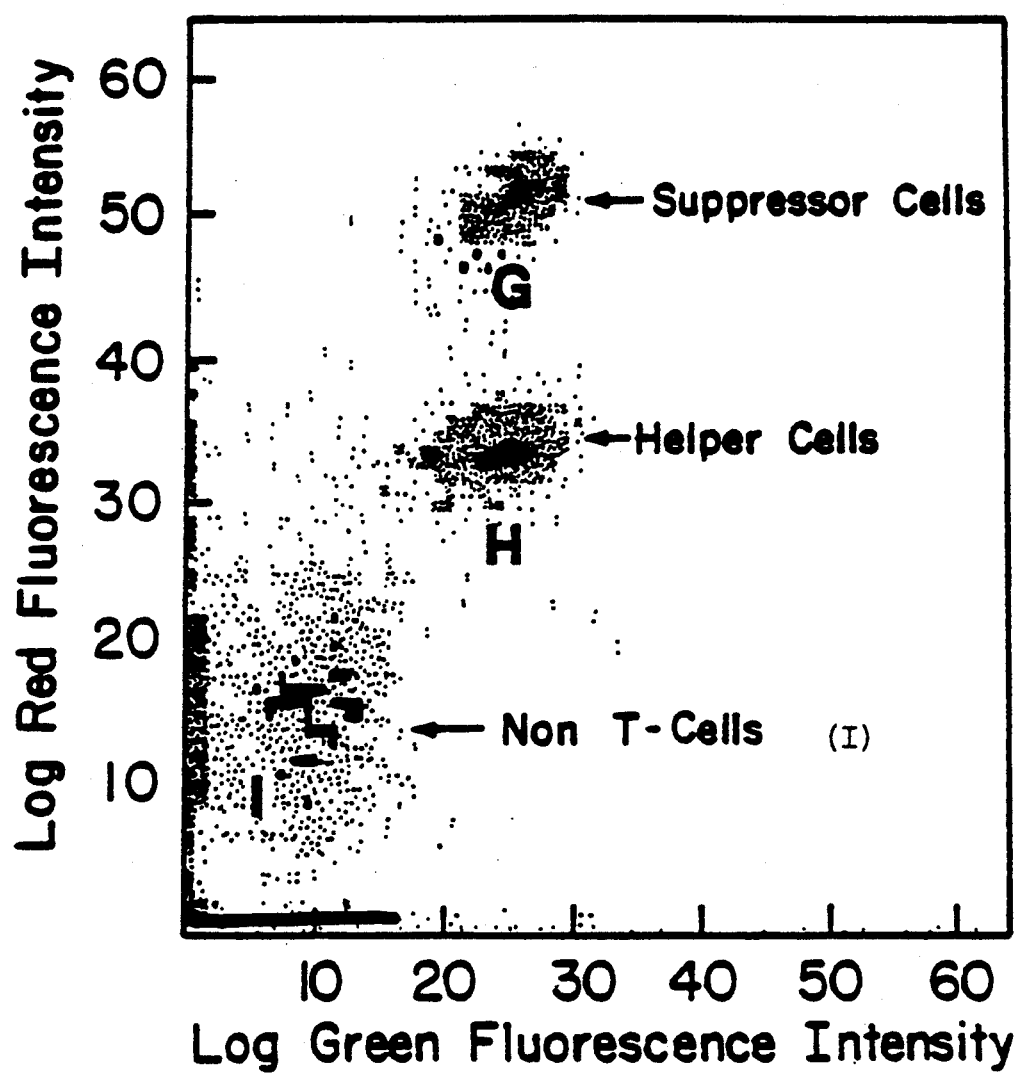
FIG. 4 is a two parameter display of the fluorescence obtained by staining a sample of mononuclear cells with undiluted phycoerythrin-conjugated antibodies to human suppressor T-cells, phycoerythrin-conjugated antibodies to human helper T-cells diluted with unconjugated antibodies to human helper T-cells, and diluted fluorescein-conjugated antibodies to human T-cells.

FIG. 4 shows a histogram produced using the invented method and two fluorochromes to distinguish two subsets of particles wherein the particles are lymphocytes. Each of the subsets, (G) and (H), has been labelled with a green-emitting fluorochrome so that the green fluorescence intensity is approximately mid-way on the fluorescence intensity scale. Subset (G) also has been saturation-labelled with a red-emitting fluorochrome and subset (H) also has been labelled with a distinguishable amount of the same red-emitting fluorochrome. Thus, subsets (G) and (H) are distinguished from the essentially unlabelled cells represented by the peak (I) near the ordinate and from each other based upon quantitative measurements of fluorescence intensity of each of the fluorochromes.

According to the invented method using two fluorochromes, an expansion of the labelling scheme used to distinguish two subsets is employed to separate five subsets. One pattern available for labelling five subsets with different amounts of two fluorochromes is:

(i) a first subset is saturation-labelled with one fluorochrome;

(ii) a second subset is saturation-labelled with a second fluorochrome;

(iii) a third subset is saturation-labelled with the first fluorochrome and saturation-labelled with the second fluorochrome;

(iv) a fourth subset is saturation-labelled with the first fluorochrome and labelled with an amount of the second fluorochrome that is distinguishable from the amount used in saturation-labelling; and (v) a fifth subset labelled with an amount of each fluorochrome that is distinguishable from the corresponding amount used in saturation-labelling with each fluorochrome.

Figure 5:
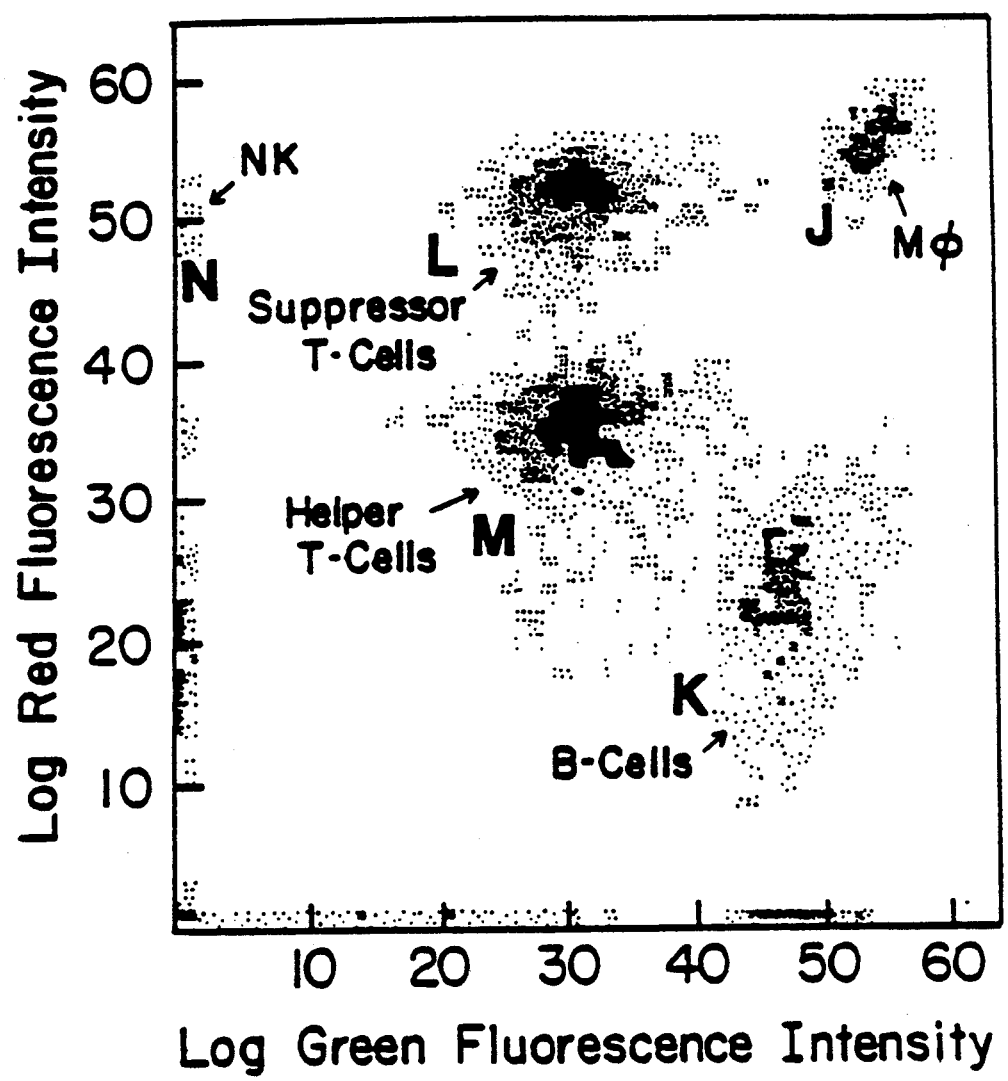
FIG. 5 is a two parameter display of the fluorescence obtained by staining a sample of mononuclear cells with undiluted fluorescein-conjugated antibodies and undiluted phycoerythrin-conjugated antibodies to human monocytes, undiluted fluorescein-conjugated antibodies to human B cells, fluorescein-conjugated antibodies to human T-cells diluted with unconjugated antibodies to human T-cells, phycoerythrin-conjugated antibodies to human suppressor T-cells, phycoerythrin-conjugated antibodies to human helper T-cells diluted with unconjugated antibodies to human helper T-cells, and phycoerythrin-conjugated antibodies to human natural-killer cells.

FIG. 5 is a histogram produced by flow cytometric analysis of five subsets of particles fluorochrome-labelled with red and green emitting fluorochromes as described above. Subset (K) is saturation-labelled with the green fluorochrome, subset (N) is saturation-labelled with the red fluorochrome, subset (J) is saturation-labelled with both fluorochromes, subset (L) is saturation-labelled with the red fluorochrome and labelled with an amount of the green fluorochrome that is distinguishable from the saturation-labelling amount, and subset (M) is labelled with an amount of each fluorochrome that is distinguishable from the corresponding saturation-labelling amount of each fluorochrome. As is seen from FIG. 5, the five subsets of particles are distinguished based upon quantitative measurements of fluorescence intensity of two fluorochromes. The area under each peak provides a measure of the number of cells in each subset.

Using the invented method with two fluorochromes, subset analysis on numbers of subsets between two and five and greater than five is performed by labelling each of the subsets with distinguishable amounts of one or both fluorochromes and using a flow cytometer to separate and count or sort the subsets based upon quantitative measurements of fluorescence intensity. As is found when using the invented method with one fluorochrome, the maximum number of subsets that can be analyzed using two fluorochromes is limited to the number of subsets that can be labelled with different amounts of the fluorochromes without causing substantial overlap in the measured fluorescence intensities for each subset. With two fluorochromes, however, the maximum number of subsets analyzable from a single sample exceeds the maximum number analyzable using one fluorochrome because subsets labelled with amounts of one fluorochrome that cause substantial overlap in measured fluorescence intensities are separated by also labelling these subsets with distinguishable amounts of a second fluorochrome.

Each of particles within each of the subsets of a sample of particles to be analyzed according to the present invention must be labelled with a similar amount of a fluorochrome or fluorochromes which amount is distinguishable from the amount of fluorochrome or fluorochromes affixed to the particles of any other subset. The types of particles which are analyzed include synthetic particles and particles of biologic origin. The method is useful to analyze microspheres produced, for example, as stated in U.S. Pat. No. 3,790,492, which is incorporated herein by reference, and to analyze other polymeric materials. Particles of biologic origin analyzed according to the invented method include blood cells and other formed elements of blood and disrupted soft tissue cells.

The method of labelling particles with fluorochrome differs depending upon the type of particle being labelled. Fluorochrome-labelled polymers such as polyvinyl chloride and polyvinyl pyrrolidine, are produced by including in the monomer mixture an amount of one or two fluorochromes sufficient, upon polymerization by standard procedures, to yield polymers having the desired amount of fluorochromes. Preferably, one of the amounts of fluorochrome added to the monomer mixture is selected so that the fluorescence intensity of the polymer produced is at or near the upper limit of fluorescence intensity detectable by the instrument and instrument settings being used. Dilutions of this amount then are used to label other polymers with a range of amounts of fluorochrome.

Biological particles, such as formed elements of blood which include red blood cells and red blood cell precursors, mononuclear cells and mononuclear cell precursors, and platelets, and other tissue cells, are fluorochrome labelled by reaction with fluorochrome-conjugated antibodies, preferably monoclonal antibodies, that have affinity for antigens on the cells of one of the subsets and do not have significant affinity for antigens on the cells of the other subsets included in the sample. Fluorochrome-conjugated monoclonal antibodies having the required specifity in cell antigen affinity are available from various manufacturers such as Becton Dickinson Immunocytometry Systems of Mountain View, Calif., Coulter Immunology of Hialeah, Fla. and others. Additionally, cell type specific antibodies are prepared according to standard monoclonal antibody techniques such as described in Kohler, G. and C. Milstein, *Continuous Cultures of Fused Cells Secreting Antibody of Predefined Specificity,* Nature 256:495 (1975). Less preferably, the specific antibodies are prepared by conventional techniques that yield polyclonal antibodies. Once produced, the specific antibodies are fluorochrome-conjugated by methods known in the art. See, e.g., The, T. H. and T. E. W. Feltkamp, *Conjugation of Fluorescein Isothiocyanate to Antibodies: I. Experiments on the Conditions of Conjugation,* Immunology 18:865 (1970); The, T. H. and T. E. W. Feltkamp, *Conjugation of Fluorescein Isothiocyanate to Antibodies: II. A Reproducible Method,* Immunology 18:875 (1970); Oi, V. T., et al., *Fluorescent Phycobiliprotein Conjugates for Analyses of Cells and Molecules,* J. Cell Biol. 93:981 (1982).

As an alternative to direct conjugation of fluorochromes to the antibody protein, the constant region of the antibodies are secured to liposomes containing selected amounts of one or two fluorochromes. Liposomes are prepared and secured to antibodies by published techniques such as described in Lesserman, L. D., Immunologic Targeting of Liposomes in *Liposomes, Drugs and Immunocompetent Cell Functions,* ed. C. Nicolau and A. Paraf, Academic Press (1981). Selected amounts of one or two fluorochromes are loaded into the liposomes by procedures known in the art. Fluorochrome-conjugating antibodies using liposomes is preferable when formulating antibodies having large amounts of fluorochrome such as would be affixed to some of the subsets analyzed using instruments that include amplifiers having a dynamic range greater than three logs.

In another alternative to direct conjugation of fluorochromes to the antibody protein, the constant region of the antibodies are linked to fluorochrome-labelled microspheres. The fluorochrome-labelled microspheres preferably are prepared as described above by incorporating into the monomer mixture a selected amount of one or two fluorochromes. Thus prepared, the fluorochrome-labelled microspheres then are linked to the antibodies by known techniques.

The sample of biological particles to be analyzed is fluorochrome-labelled using standard immunofluorescence techniques by adding to the sample one or more fluorochrome-conjugated antibodies that individually have affinity for specific antigens on the cells of the subsets within the sample that is to be separated. The fluorochrome-conjugated antibodies are selected so that each subset is labelled with distinguishable fluorochrome amounts, that is no two subsets are labelled with indistinguishable amounts of both fluorochromes. Any two subsets labelled with indistinguishable amounts of one fluorochrome must be labelled with distinguishable amounts of the second fluorochrome.

Multiple subsets preferably are analyzed by saturation-labelling one subset with one of the fluorochromes, saturation-labelling a second subset with a second fluorochrome, and saturation labelling a third subset with each of the fluorochromes. Additional subsets are labelled with one or both of the fluorochromes so that they are distinguishable based upon quantitative measurements of the fluorescence intensity of at least one of the fluorochromes.

Saturation labelling of those subsets in the sample of particles that are labelled with the one fluorochrome optimally is performed by mixing the sample with an excess concentration of fluorochrome-conjugated antibodies having affinity for the antigens specific for particles of that subset. Saturation labelling of the particles of those subsets that are labelled with two fluorochromes optimally is performed by mixing the sample with an excess concentration of first fluorochrome-conjugated antibodies having specific affinity for antigens on the cells of the subset and an excess concentration of second antibodies having specific affinity for antigens on the cells of the subset, which second antibodies are conjugated to a different fluorochrome.

Labelling of those subsets that are less than saturation-labelled with one or both fluorochromes preferably is performed by mixing the sample with a concentration of fluorochrome-conjugated antibodies less than that used for saturation labelling and that labels the cells of the subset with an amount of fluorochrome that is distinguishable from the amount of fluorochrome affixed to any other subset of particles. To label a subset of cells with less than saturation-labelling amounts of two antibodies conjugated to different fluorochromes, the antibody concentrations must be selected so that no two subsets of cells are labelled with indistinguishable amounts of both fluorochromes. Because antibody binding to the cells is more consistent and predictable when the binding is performed under conditions of antibody excess, the less than saturation-labelling concentrations of fluorochrome-conjugated antibodies ideally are prepared by diluting the fluorochrome-conjugated antibodies with non fluorochrome-conjugated antibodies having the same antigenic affinity so that the resulting antibody concentration exceeds that needed to bind all available antibody binding sites on particles of the subset.

An alternative method for labelling subsets of biologic particles with less than saturation-labelling amounts of one or two fluorochromes is to vary the number of fluorochrome molecules affixed to each molecule of antibody. The maximum number of fluorochrome molecules attached to each antibody molecule is selected so that when biologic particles are reacted with an excess amount of fluorochrome-conjugated antibodies, the particles are labelled with an amount of fluorochrome that renders the fluorescence intensity of the particles at or near the maximum fluorescence intensity measureable by the instrument and instrument settings being used. Particles of the remaining subsets in the sample are labelled with distinguishable fluorochrome amounts by reacting those particles with antibody molecules bearing lesser numbers of fluorochrome molecules. Differences in number of fluorochrome molecules affixed to each antibody molecule are achieved using standard techniques that include varying the fluorochrome concentration in the mixture used to form the fluorochrome-conjugated antibodies and varying the time period that the antibodies being fluorochrome-conjugated are exposed to the fluorochrome-containing mixture.

Various fluorochromes are used in the present invention. Such fluorochromes include fluorescein, rhodamine, Texas red, various cyanine dyes including indocarbocyanines, indodicarbocyanines, oxadicarbocyanine, thiocarbocyanines, thiodicarbocyanines, merocyanine 540, and safranin O, and sulforhodamine. Additionally, the fluorochromes used in this invention include phycobiliproteins such as phycoerythrin, allophycocyanin, and others listed in U.S. Pat. No. 4,520,110 which is incorporated herein by reference. In a preferred embodiment of the invention using two fluorochromes, the fluorochromes are selected so that their excitation wavelengths fall within the range of wavelengths that are produced by a single light source, thus enabling the use of less sophisticated single laser flow cytometers and other single light source instruments.

The invention includes reagents used to fluorochrome label the particles analyzed according to the invented method. The reagent used to perform subset analysis of biologic cells using one fluorochrome is comprised of several fluorochrome-conjugated antibodies each having affinity for antigens specific to the cells of one of the subsets. Each of the fluorochrome-conjugated antibodies is present in the reagent in different concentrations selected so that each subset of cells is labelled with distinguishable amounts of the fluorochrome. Sub-maximal fluorochrome labelling of the cells preferably is achieved by including in the reagent a sufficient quantity of non fluorochrome-conjugated antibodies identical in antigen affinity to the fluorochrome-conjugated antibodies the non-conjugated antibodies are being used to dilute to form fluorochrome-conjugated antibody concentrations that result in labelling each subset with a distinguishable amount of fluorochrome.

Thus, a reagent used to analyze two subsets with one fluorochrome using the present invention includes, for example, a concentration of fluorochrome-conjugated antibodies having affinity for antigens specific to the cells of one subset sufficient to saturation label those cells and fluorochrome-conjugated antibodies having affinity for antigens specific to the cells of the second subset diluted with an amount of those same antibodies unconjugated to fluorochrome sufficient to result in a concentration of the second subset cell specific antibodies being approximately one-half to two-thirds the concentration of the first subset cell specific antibodies. Reagents used to analyze a greater number of subsets are prepared by including progressive dilutions of fluorochrome-conjugated antibodies to each of the subsets. The concentrations of fluorochrome-conjugated antibodies included in the reagent, however, must be sufficiently different to label the cells of each subset with an amount of fluorochrome label that is distinguishable from each of the other subsets.

Alternatively, a reagent used to analyze two subsets with one fluorochrome includes, for example, antibodies specific to one subset conjugated to a sufficient number of fluorochrome molecules so that reacting the subset of particles with the antibodies under conditions of antibody excess yields saturation-labelled particles and antibodies specific to the second subset conjugated to a lesser number of fluorochrome molecules so that reaction under similar conditions produces particles having approximately one-half to two-thirds saturation-labelling fluorochrome amounts. Additional numbers of subsets are analyzed using reagents having subset specific antibodies conjugated to progressively fewer numbers of fluorochrome molecules provided that no two groups of subset specific antibodies are conjugated to amounts of fluorochrome that render subsets labelled with such antibodies indistinguishable.

The preferable reagents used in performing subset analysis on biological particles with two fluorochromes preferably include various concentrations of fluorochrome-conjugated antibodies selected so that using the reagent to label the cells produces no two subsets of cells that contain indistinguishable amounts of both fluorochromes. The reagent, therefore, contains concentrations of fluorochrome antibodies selected so that upon mixing with the reagent all subsets labelled with indistinguishable amounts of one fluorochrome are labelled with distinguishable amounts of the remaining fluorochrome. The various concentrations of fluorochrome-conjugated antibodies included in the reagent preferably are prepared by diluting the fluorochrome-conjugated antibodies with non-conjugated antibodies of like antigenic specificity.

One pattern of fluorochrome-conjugated antibody concentrations included in a two fluorochrome reagent designed for subset analysis is:

i) antibodies having affinity for antigens specific for particles of one subset conjugated with the first fluorochrome;

ii) antibodies having affinity for antigens specific for particles of a second subset conjugated with the second fluorochrome;

iii) antibodies having affinity for antigens specific for particles of a third subset conjugated to the first fluorochrome, and antibodies having affinity for antigens specific for particles of the third subset conjugated to the second fluorochrome diluted approximately equally with unconjugated antibodies of like antigenic affinity; and iv) antibodies having affinity for antigens specific to particles of a fourth subset conjugated to the first fluorochrome diluted approximately equally with unconjugated antibodies of like antigenic affinity, and antibodies having affinity for antigens specific to particles of the fourth subset conjugated to the second fluorochrome diluted approximately equally with unconjugated antibodies of like antigenic affinity.

This reagent is added to a sample of cells in sufficient quantity so that each of the differently antigen specific antibodies is present in sufficient amount to exceed that needed to label all available antigen-binding sites. Reagents for analyzing a greater number of subsets are prepared in a similar manner using progressive dilutions of the fluorochrome-conjugated antibodies limited by the requirement that the concentrations of fluorochrome-conjugated antibodies be sufficiently different so that when added to a population of cells no two subsets of cells are labelled with indistinguishable amounts of both fluorochromes.

Alternatively, a reagent containing two fluorochromes includes appropriately selected subset specific antibodies conjugated to different numbers of fluorochrome molecules so that upon reaction with the fluorochrome-conjugated antibodies no two subsets are labelled with indistinguishable amounts of both fluorochromes.

The invention further includes fluorochrome-labelled particles used as standards to monitor operation of the instruments used in performing subset analysis and to detect variations in the number of antibody binding sites in different samples of biologic tissues. The types of particles used include liposomes and synthetic polymeric materials such microspheres. The microspheres and liposomes are prepared and fluorochrome-labelled as described above. The fluorochrome or fluorochromes used to label the particles are selected so that they have excitation and emission spectra similar to the fluorochrome or fluorochromes used to label the sample for which the particles are being used as standards. Preferably, the fluorochrome or fluorochromes used to label the particles are stable under refrigeration or in a standard preservative solution containing, for example, benzyl alcohol or benzalkonium chloride. The particles used as standards preferably are selected such that the low angle light intensity, the ninety degree angle light intensity, and the size are different from the particles contained in the sample to be analyzed following standardization.

To monitor an instrument used in subset analysis or to detect sample-to-sample variations in the number of antibody binding sites, a mixture of two or more subsets of standard particles labelled with distinguishable amounts of one or two fluorochromes is prepared. The number of subsets and fluorescence intensities of the subsets of standard particles preferably are selected so that they approximate the number of subsets and fluorescence intensities of the particles in the sample to be analyzed subsequently. The mixture of standard particles then is added to the sample to be analyzed and analyzed along with the sample. Alternatively, the mixture of standard particles is analyzed in sequence with the particles of the sample.

The following examples are illustrative of the presently invented method and reagents used with the method. The examples are presented to describe the invention rather than to limit its scope as defined above and claimed below.

EXAMPLE 1

Isolation of Nucleated Blood Cells

In each of the examples below wherein the subsets analyzed are nucleated blood cells, the following procedure was utilized to separate the nucleated cells from the remaining constituents of blood.

Human blood from normal volunteers was collected by phlebotomy from a peripheral vein using a sodium heparin-containing evacuated container obtained from Vacutainer Systems of Rutherford, New Jersey. The blood was obtained from four persons and nucleated cells were isolated by layering approximately 8 ml. of whole blood on 5 ml. of a sodium metrizoate/Ficoll separation medium (Lymphoprep; Nyegaard and Company, Oslo, Norway). Ficoll is an inert, non-ionized synthetic, high polymer made by crosslinking epichlorhydrin and sucrose used as a density gradient. Tubes containing the whole blood and separation medium were centrifuged at 400 x gravity for 40 minutes at 20° Celcius (C.). Then the interface layer was withdrawn and washed twice in a Dulbecco's phosphate-buffered saline solution, pH 7.2, containing 1% bovine serum albumin and 0.05% sodium azide (PBS-BSA-AZ buffer). The cells were resuspended in the buffer, counted using a flow cytometer and standard particle counting techniques such as Coulter counting, and adjusted to a final concentration of $2 \times 10^7$ cells/ml. Using propidium iodide staining, greater than 95% of the cells were found viable.

EXAMPLE 2

Flow Cytometric Analysis

All analyses using a flow cytometer referred to in the following examples were performed using an EPICS 753 flow cytometer manufactured by Coulter Electronics of Hialeah, Fla. When using the fluorochromes phycoerythrin and/or fluorescein, 500 mw of light at an exciting wavelength of 488 nm was utilized. Also, a 488 nm dichroic mirror and 488 nm band pass for the right angle light scatter signal, a 515 nm interference filter and 515 nm long pass filter to block the excitation wavelength, a 560 nm dichroic mirror to split the fluorescein/phycoerythrin signal, a 590 nm longpass filter for the phycoerythrin signal, a 525 nm bandpass filter for the fluorescein signal, and a 1.5 OD filter for the forward angle light scatter signal were employed. When mononuclear cells were analyzed, gates were set around these cells using right angle light scatter and forward angle light scatter to remove any clumps or debris.

EXAMPLE 3

Fluorochrome-labelling of Biologic Particles

All biologic particles were fluorochrome-labelled by mixing a sample containing the particles with fluorochrome-conjugated antibodies having affinity for antigens specific to the particles of a subset of interest. Fluorochrome-conjugated and unconjugated monoclonal antibodies were purchased from commercial producers.

All labelling of cells was done under standard immunofluorescent staining conditions in 96-well V bottom plates at 4° C. Control wells were set using appropriate unconjugated antibodies or combinations thereof brought to final volume by addition of PBS-BSA-AZ buffer. Fifty microliters of cell suspension containing approximately $1 \times 10^6$ cells was added to each well with appropriate amounts of fluorochrome and samples were incubated for 30 minutes.

After incubation, first 50 µl of PBS-BSA-AZ buffer and then 20 µl of fetal calf serum were added to each well and the plates were centrifuged at 400× gravity for 10 minutes at 4° C. Following supernatant removal, the cell pellets were resuspended in 200 µl of PBS-BSA-AZ.

EXAMPLE 4

Analysis of Two Subsets From a Single Sample Using One Fluorochrome

Using phycoerythrin-conjugated monoclonal antibodies, two subsets of mononuclear cells were analyzed from a sample of mononuclear cells prepared from human blood. The subsets analyzed were suppressor T-cells and helper T-cells. The subsets were labelled with a reagent containing phycoerythrin-conjugated anti-Leu-2a monoclonal antibodies which are specific to human suppressor T-cells, and phycoerythrin-conjugated and unconjugated anti-Leu-3a monoclonal antibodies which are specific to human helper T-cells. The phycoerythrin-conjugated and unconjugated antibodies were obtained from Becton-Dickinson Immunocytometry Systems, Mountain View, Calif.

The phycoerythrin-conjugated anti-Leu-2a antibodies were obtained in a concentration of 25 µg purified immunoglobulin/ml. and used without dilution. Phycoerythrin anti-Leu-3a antibodies obtained in a concentration of 25 µg purified immunoglobulin/ml. were diluted with unconjugated anti-Leu-3a antibodies in a concentration of 100 µg purified immunoglobulin/ml. prior to use. The anti-Leu-3a antibodies were diluted by adding 1.5 µl of the unconjugated antibody preparation to 13 µl of the phycoerythrin-conjugated antibody preparation. The cell-labelling reagent contained 20 µl of the phycoerythrin-conjugated anti-Leu-2a preparation, 15 µl of the diluted phycoerythrin-conjugated anti-Leu-3a preparation, and sufficient PBS-BSA-AZ buffer to bring the total volume to 80 µl.

FIG. 3 is a graph of the results obtained by quantitative measurement of fluorescence intensity of the labelled mononuclear cells using a flow cytometer equipped with a three-log dynamic amplifier and standard particle counting techniques. The peak (F) represents the helper T-cells labelled with the diluted phycoerythrin-conjugated antibodies and the peak (E) represents the suppressor T-cells labelled with undiluted phycoerythrin-conjugated antibodies. The area under each of the peaks is a measure of the number of cells in each of the subsets.

FIG. 3 presents the results obtained by quantitative measurement of fluorescence intensity and demonstrates that the suppressor T-cells (E) were labelled with an amount of fluorochrome that renders the fluorescence intensity of these cells very near the upper limit measurable by the instrument at the settings utilized. As is indicated by the position of the peak (F) on the fluorescence intensity axis, the helper T-cells were labelled with an amount of fluorochrome that rendered the fluorescence intensity of these cells approximately two-thirds that of the suppressor T-cells.

Preferably, however, the helper T-cells and suppressor T-cells are fluorochrome-labelled so that the relative fluorescence intensities of these subsets is reversed. This alternate labelling is achieved by reacting the sample of mononuclear cells with a sufficient amount of undiluted phycoerythrin-conjugated anti-Leu-3a antibodies and appropriately diluted phycoerythrin-conjugated anti-Leu-2a antibodies so that the suppressor T-cells are labelled with an amount of fluorochrome greater than and distinguishable from the amount with which the helper T-cells are labelled. Thus labelled, the peaks representing the helper T-cells and suppressor T-cells appear on the fluorescence intensity scale in reverse order from that shown in FIG. 3.

Thus, using one fluorochrome the helper T-cells and suppressor T-cells are separated based upon quantitative distinctions of red fluorescence intensity.

EXAMPLE 5

Analysis of Three Subsets From a Single Sample Using One Fluorochrome

Using fluorescein-conjugated monoclonal antibodies, three subsets of cells are analyzed from a sample of human blood mononuclear cells. Monocytes, suppressor T-cells, and helper T-cells are the subsets analyzed. The monocytes are labelled with monocyte-specific antibodies covalently linked to liposomes which contain fluorescein immobilized in the liposome. The amount of fluorescein in the liposomes is selected so that the fluorescence intensity of the labelled monocytes is not greater than the maximum intensity measurable by a standard flow cytometer equipped with a six-log dynamic amplifier and approximately twice that of the suppressor T-cells. The suppressor T-cells are labelled with fluorescein-conjugated anti-Leu-2a antibodies which result in these cells having fluorescence intensities approximately one-half that of the monocytes. The helper T-cells are labelled with fluorescein-conjugated anti-Leu-3a antibodies diluted with sufficient unconjugated anti-Leu-3a antibodies so that the fluorescence intensities of the helper T-cells are approximately one-half that of the suppressor T-cells.

Then the sample of cells is passed through a standard flow cytometer having a six log dynamic amplifier which segregates and counts the cells of each subset. Labelling the sample of cells as described in this example results in the monocytes having the highest fluorescence intensity, the suppressor T-cells having intermediate fluorescence intensity, and the helper T-cells having the lowest fluorescence intensity with no substantial overlap in the fluorescence intensities of any two subsets.

EXAMPLE 6

Analysis of Two Subsets From A Single Sample Using Two Fluorochromes

Using phycoerythrin-conjugated and fluorescein-conjugated antibodies, two subsets of mononuclear cells were analyzed from a sample of mononuclear cells prepared from human blood. The subsets analyzed were suppressor T-cells and helper T-cells. The subsets were labelled with a reagent containing phycoerythrin-conjugated anti-Leu-2a monoclonal antibodies which are specific to human suppressor T-cells, phycoerythrin-conjugated anti-Leu-3a monoclonal antibodies which are specific to human helper T-cells diluted with unconjugated antibodies of like antigenic affinity, and fluorescein-conjugated anti-Leu-4 antibodies which are specific to human T-cells diluted with unconjugated antibodies of like antigenic affinity. As indicated in Example 4, preferably the red fluorescence intensities of the suppressor and helper T-cells is reversed. All of the fluorochrome-conjugated and unconjugated antibodies were obtained from Becton-Dickinson Immunocytometry Systems, Mountain View, Calif.

The phycoerythrin-conjugated anti-Leu 2a antibodies were obtained in a concentration of 25 $\mu g$ purified immunoglobulin/ml. and used without dilution. Phycoerythrin-conjugated anti-Leu-3a antibodies obtained in a concentration of 25 $\mu g$ purified immunoglobulin/ml. were diluted with unconjugated anti-Leu-3a antibodies obtained in a concentration of 100 $\mu g$ purified immunoglobulin/ml by adding 1.5 $\mu l$ of the unconjugated antibody preparation to 13 $\mu l$ of the phycoerythrin-conjugated antibody preparation. Fluorescein-conjugated anti-Leu-4 antibodies obtained in a concentration of 100 $\mu g$ purified immunoglobulin/ml were diluted with unconjugated anti-Leu-4 antibodies obtained in a concentration of 200 $\mu g$ purified immunoglobulin/ml by adding 3 $\mu l$ of the fluorescein-conjugated antibody preparation to 1 $\mu l$ of the unconjugated antibody preparation.

The cell-labelling reagent contained 20 $\mu l$ of the phycoerythrin-conjugated anti-Leu-2a preparation, 15 $\mu l$ of the diluted phycoerythrin-conjugated anti-Leu-3a preparation, 5$\mu l$ of the diluted fluorescein-conjugated anti-Leu-4 preparation, and sufficient PBS-BSA-AZ buffer to bring the total volume to 80 $\mu l$.

FIG. 4 displays quantitative measurements of fluorescence intensity of the subsets of T-cells stained with the reagent of this example. On one axis green fluorescence is displayed; on the other axis red fluorescence is displayed. The helper T-cells and suppressor T-cells have approximately equivalent green fluorescence intensity, but have red fluorescence intensities sufficiently different so that the red fluorescence intensities of the suppressor T-cells do not overlap significantly with the red fluorescence intensities of the helper T-cells. Thus, based on quantitative measurements of fluorescence intensity made by a standard flow cytometer, the suppressor T-cells and helper T-cells, having similar green fluorescence intensities, are separated based upon quantitative differences in red fluorescence intensities.

EXAMPLE 7

Analysis of Five Subsets From a Single Sample Using Two Fluorochromes

Using seven different monoclonal antibodies, some conjugated to either phycoerythrin or fluorescein and some unconjugated, five subsets of human mononuclear cells were analyzed from a single sample of mononuclear cells using quantitative fluorescence intensity measurements as the distinguishing parameter. The subsets analyzed were suppressor T-cells, helper T-cells, natural-killer cells, monocytes, and B-cells. Fluorescein-conjugated B1 antibodies to human B-cells and fluorescein-conjugated Mo2 antibodies to human monocytes were obtained from Coulter Immunology. The remaining antibodies were obtained from Becton-Dickinson Immunocytometry Systems.

The following antibody preparations were employed in labelling the five subsets with distinguishable fluorochrome amounts. The undiluted preparations were used as obtained from the manufacturers after reconstitution according to the manufacturers directions.

i) Phycoerythrin-conjugated anti-Leu-11c antibodies specific to human natural killer cells in a concentration of 50 $\mu g$ purified immunoglobulin/ml;

ii) Fluorescein-conjugated anti-B1 antibodies specific to human B lymphocytes in an antibody concentration such that 5 $\mu l$ is sufficient to saturation-label $1 \times 10^6$ cells in a reaction volume of 100–200 $\mu l$;

iii) Fluorescein-conjugated anti-Mo2 antibodies specific to human monocytes in an antibody concentration such that 5 $\mu l$ is sufficient to saturation-label $1 \times 10^6$ cells in a reaction volume of 100–200 $\mu l$;

iv) Phycoerythrin-conjugated anti-Leu-M3 antibodies specific to human monocytes in a concentration such that 20 $\mu l$ is sufficient to saturation-label $1 \times 10^6$ cells in 100–200 $\mu l$ reaction volume;

v) Diluted fluorescein-conjugated anti-Leu-4 antibodies specific to human T-lymphocytes prepared by adding 3 $\mu l$ of conjugated antibodies having a concentration of 100 $\mu g$ purified immunoglobulin/ml to 1 $\mu l$ of unconjugated anti-Leu-4 antibodies having a of 200 $\mu g$ purified immunoglobulin/ml;

vi) Phycoerythrin-conjugated anti-Leu-2a antibodies specific to human suppressor T-cells in a concentration of 25 $\mu g/ml$ purified immunoglobulin/ml; and vii) Diluted phycoerythrin-conjugated anti-Leu-3a antibodies specific to human helper T-cells prepared by adding 13.0 $\mu l$ of conjugated antibodies having a concentration of 25 $\mu g$ purified immunoglobulin/ml to 1.5 $\mu l$ of unconjugated anti-Leu-3a antibodies having a concentration of 100 $\mu g$ purified immunoglobulin/ml The reagent utilized in differentially labelling the five mononuclear cell subsets included the following amounts of the above antibody preparations:

i) 20 $\mu l$ of the phycoerythrin-conjugated anti-Leu-11c;

ii) 5 $\mu l$ of the fluorescein-conjugated anti-B1;

iii) 5 $\mu l$ of the fluorescein-conjugated anti-Mo2;

iv) 20 $\mu l$ of the phycoerythrin-conjugated anti-Leu-M3;

v) 5 $\mu l$ of the diluted fluorescein-conjugated anti-Leu-4;

vi) 20 μl of the phycoerythrin-conjugated anti-Leu-2a; and vii) 15 μl of the diluted phycoerythrin-conjugated anti-Leu-3a.

After labelling a sample of human mononuclear cells with this reagent, the sample was passed, for analysis, through a standard single laser flow cytometer equipped with a three-log dynamic range amplifier. FIG. 5 is the histogram of the five subsets separated from the sample. From FIG. 5 it is seen that the subsets were segregated in two dimensions by plotting quantitative measurements of the fluorescence intensity of the green fluorochrome (fluorescein) on one axis and quantitative measurements of the fluorescence intensity of the red fluorochrome (phycoerythrin) on the other axis. Using these measurements no two subsets overlaped sufficiently to render them indistinguishable. The cells of the suppressor T-cell and helper T-cell subsets represented by peaks (L) and (M), respectively, were labelled with similar amounts of fluorescein, but nevertheless were distinguishable because these cells were labelled with distinguishable amounts of phycoerythrin. As stated in Example 4, preferably, the suppressor T-cells and helper T-cells are phycoerythrin-labelled so that the relative red fluorescence intensities of these two subsets is reversed from that shown in this example.

EXAMPLE 8

Analysis of Seven Subsets From a Single Sample Using Two Fluorochromes

Using nine different monoclonal antibodies, some conjugated to either phycoerythrin or fluorescein, and some unconjugated, seven subsets of human nucleated blood cells are analyzed from a single sample of nucleated blood cells using quantitative fluorescence intensity measurements as the distinguishing parameter. The subsets analyzed are suppressor T-cells, helper T-cells, natural-killer cells, monocytes, B-cells, band cells, and mature neutrophils.

In labelling the subsets with distinguishable fluorochrome amounts, fluorescein-conjugated B1 antibodies to human B-cells, and fluorescein-conjugated Mo2 antibodies to human monocytes obtained from Coulter Immunology are used. The remaining antibodies, except those to the band cells and neutrophils, are obtained from Becton-Dickinson Immunocytometry Systems. Antibodies to the band cells and to all neutrophils are prepared using standard monoclonal antibody techniques. One of the antibodies has affinity for antigens specific to all neutrophils, including band cells, (SK&F-MAB-101) and the second of the antibodies has affinity for antigens specific to the band cells only (SK&F-MAB-102). Additionally, the antibodies to the neutrophils and band cells are selected so that they do not compete for binding to the same antigenic determinant and so that neither of the antibodies substantially reduces the affinity of the other antibody for its target antigen. SK&F-MAB-101 is conjugated directly to fluorescein containing liposomes and SK&F-MAB-102 is conjugated directly to phycoerythrin.

The following antibody preparations are used as the reagent in labelling the seven subsets with distinguishable fluorochrome amounts. Antibodies to the suppressor T-cells, helper T-cells, T-cells, natural-killer cells, monocytes, and B-cells are used as described in Example 7. SK&F-MAB-101 antibodies are conjugated directly to liposomes containing an amount of fluorescein that renders the green fluorescence intensity of the neutrophils approximately twice that of the monocytes. SK&F-MAB-102 is conjugated to an amount of phycoerythrin that renders the red fluorescence intensity of the band cells approximately equivalent to that of the monocytes.

After labelling the sample of human nucleated blood cells with the reagent containing fluorochrome-conjugated monoclonal antibodies, the sample is passed, for analysis, through a standard single laser flow cytometer equipped with a six-log dynamic range amplifier. The histogram produced by this analysis is similar to that shown in FIG. 5, except that the green fluorescence intensity axis has a wider dynamic range and the peak representing the neutrophils appears as the most intensely labelled peak on the green axis, and the peak representing the band cells has approximately the same green fluorescence intensity as the neutrophils and approximately the same red fluorescence intensity as the monocytes.

In this example, the light scatter gates on the instrument used are set to include mononuclear and polynuclear leukocytes and to exclude red blood cells and platelets. As stated in Example 4, preferably, the suppressor T-cells and helper T-cells are phycoerythrin-labelled so that the relative red fluorescence intensities of these two subsets is reversed from that shown in this example.

EXAMPLE 9

Using Fluorochrome-Labelled Particles as Standards

A mixture of microspheres used as standards in association with analysis of five subsets as described in Example 7 contains:

i) microspheres labelled with an amount of 1,1'-didodecylcycloxacarbocyanine (DiO-C(12)-3) sufficient to render the green fluorescence intensity of these microspheres indistinguishable from fluorochrome-labelled B cells from normal donors;

ii) microspheres labelled with an amount of sulforhodamine sufficient to render the red fluoresence intensity of these microspheres indistinguishable from fluorochrome-labelled natural-killer cells from normal donors;

iii) microspheres labelled with an amount of DiO-C(12)-3 and sulforhodamine sufficient to render the green and red fluorescence intensities of these microspheres indistinguishable from fluorochrome-labelled monocytes from normal donors;

iv) microspheres labelled with an amount of DiO-C(12)-3 and sulforhodamine sufficient to render the green and red fluorescence intensities of these microspheres indistinguishable from fluorochrome-labelled suppressor T-cells from normal donors; and v) microspheres labelled with an amount of DiO-C(12)-3 and sulforhodamine sufficient to render the green and red fluoresence intensities of these microspheres indistinguishable from fluorochrome-labelled helper T-cells from normal donors.

After adding the mixture of microspheres to a sample of human mononuclear cells, the sample is passed, for analysis, through a standard single laser flow cytometer equipped with a three-log dynamic range amplifier. The histogram produced upon such analysis is similar to that shown in FIG. 5. Alternatively, the microspheres are passed through the flow cytometer just prior to passage of the sample of mononuclear cells and the operation of the flow cytometer is monitored by comparing the histogram produced upon analysis of the microspheres to the histogram produced upon analysis of the sample of cells.

While the preferred embodiments of the invention are illustrated by the above, it is to be understood that the invention is not limited to the precise instructions herein disclosed and extends to all modifications that fall within the scope of the following claims.

What is claimed is:

1. A method for distinguishing at least two subpopulations of biologic particles in a sample comprising the steps of
    a. selecting a first reagent that comprises:
        a first amount of a first labelled antibody that is labelled solely with a first fluorochrome, or
        a mixture of the first amount of the first labelled antibody and a first unlabelled antibody that is free of any fluorochrome,
        wherein the first labelled antibody and the first unlabelled antibody have the same antigen specificity and are specifically reactive to a first subpopulation biologic particle in the same, and
        wherein the first labelled antibody, or the first labelled antibody and the first unlabelled antibody, are present in a quantity sufficient to obtain maximum binding to the first subpopulation biologic particle and sufficient to confer upon the first subpopulation biologic particle a first fluorescence intensity,
    b. selecting a second reagent that comprises:
        a second amount of a second labelled antibody that is labelled solely with the first fluorochrome, or
        a mixture of the second amount of the second labelled antibody and a second unlabelled antibody that is free of any fluorochrome,
        wherein the second labelled antibody and the second unlabelled antibody have the same antigen specificity and are specifically reactive to a second subpopulation biologic particle in the sample, and
        wherein the second labelled antibody, or the second labelled antibody and the second unlabelled antibody, are present in an quantity sufficient to obtain maximum binding to the second subpopulation biologic particle and sufficient to confer upon the second subpopulation biologic particle a second fluorescence intensity,
        wherein the first and second amounts of the labelled antibodies are adjusted, relative to each other, so that one subpopulation biologic particle is distinguished from another subpopulation biologic particle based upon the difference in their fluorescence intensities,
    c. mixing the reagents with the sample,
    d. inducing fluorescence of the fluorochrome, and
    e. quantitatively measuring the intensity of fluorescence of each biologic particle in the sample.

2. The method for distinguishing at least two subpopulations of biologic particles in a sample as claimed in claim 1, further comprising, between steps (b) and (c), the additional step of selecting a third reagent that comprises:
    a third amount of a third labelled antibody that is labelled solely with a first fluorochrome, or
    a mixture of the third amount of the third labelled antibody and a third unlabelled antibody that is free of any fluorochrome,
    wherein the third labelled antibody and the third unlabelled antibody have the same antigen specificity and are specifically reactive to a third subpopulation biologic particle in the sample,
    wherein the third labelled antibody, or the third labelled antibody and the third unlabelled antibody, are present in a quantity sufficient to obtain maximum binding to the third subpopulation biologic particle and sufficient to confer upon the third subpopulation biologic particle a third fluorescence intensity, and
    wherein the third amount of the third labelled antibody is adjusted, relative to the first and second amounts of labelled antibodies, so that the third fluorescence intensity is different from the first and second fluorescence intensities.

3. The method for distinguishing at least two subpopulation of biological particles in a sample as claimed in claim 2, further comprising, between steps (b) and (c), the additional step of selecting a fourth reagent that comprises:
    a fourth amount of a fourth labelled antibody that is labelled solely with the first fluorochrome, or
    a mixture of the fourth amount of the fourth labelled antibody and a fourth unlabelled antibody that is free of any fluorochrome,
    wherein the fourth labelled antibody and the fourth unlabelled antibody have the same antigen specificity and are specifically reactive to a fourth subpopulation biologic particle in the sample,
    wherein the fourth labelled antibody, or the fourth labelled antibody and the fourth unlabelled antibody, are present in a quantity sufficient to obtain maximum binding to the fourth subpopulation biologic particle and sufficient to confer upon the fourth subpopulation biologic particle a fourth fluorescence intensity, and
    wherein the fourth amount of the fourth labelled antibody is adjusted, relative to the first, second, and third amounts of labelled antibodies, so that the fourth fluorescence intensity is different from the first, second, and third fluorescence intensities.

4. The method for distinguishing at least two subpopulations of biologic particles in a sample as claimed in claim 3, further comprising, between steps (b) and (c), the additional step of selecting a fifth reagent that comprises:
    a fifth amount of a fifth labelled antibody that is labelled solely with the first fluorochrome, or
    a mixture of the fifth amount of the fifth labelled antibody and a fifth unlabelled antibody that is free of any fluorochrome,
    wherein the fifth labelled antibody and the fifth unlabelled antibody have the same antigen specificity and are specifically reactive to a fifth subpopulation biologic particle in the sample,
    wherein the fifth labelled antibody, or the fifth labelled antibody and the fifth unlabelled antibody, are present in a quantity sufficient to obtain maximum binding to the fifth subpopulation biologic particle and sufficient to confer upon the fifth subpopulation biologic particle a fifth fluorescence intensity, and
    wherein the fifth amount of the fifth labelled antibody is adjusted, relative to the first, second, third and fourth amounts, so that the fifth fluorescence intensity is different from the first, second, third, and fourth fluorescence intensities.

5. The method for distinguishing at least two subpopulations of biologic particles in a sample as claimed in claim 1, further comprising, between steps (b) and (c), the additional step of selecting a first additional reagent that comprises:

a first amount of a first additional labelled antibody that is labelled solely with a second fluorochrome, or a mixture of the first amount of the first additional labelled antibody and a first additional unlabelled antibody that is free of any fluorochrome, wherein the first additional labelled antibody and the first additional unlabelled antibody have the same antigen specificity and are specifically reactive to a first additional subpopulation biologic particle in the sample, wherein the first additional labelled antibody, or the first additional labelled antibody and the first additional unlabelled antibody, are present in a quantity sufficient to obtain maximum binding to the first additional subpopulation biologic particle and sufficient to confer upon the first additional subpopulation biologic particle a first additional fluorescence intensity, and wherein the first and second fluorochromes are inducible to fluoresce at different wave lengths.

6. The method for distinguishing at least two subpopulations of biologic particles in a sample as claimed in claim 2, further comprising, between steps (b) and (c), the additional step of selecting a first additional reagent that comprises:

a first amount of a first additional labelled antibody that is labelled solely with a second fluorochrome, or a mixture of the first amount of the first additional labelled antibody and a first additional unlabelled antibody that is free of any fluorochrome, wherein the first additional labelled antibody and the first additional unlabelled antibody have the same antigen specificity and are specifically reactive to a first additional subpopulation biologic particle in the sample, wherein the first additional labelled antibody, or the first additional labelled antibody and the first additional unlabelled antibody, are present in a quantity sufficient to obtain maximum binding to the first additional subpopulation biologic particle and sufficient to confer upon the first additional subpopulation biologic particle a first additional fluorescence intensity, and wherein the first and second fluorochromes are inducible to fluoresce at different wave lengths.

7. The method for distinguishing at least two subpopulations of biologic particles in a sample as claimed in claim 3, further comprising, between steps (b) and (c), the additional step of selecting a first additional reagent that comprises:

a first amount of a first additional labelled antibody that is labelled solely with a second fluorochrome, or a mixture of the first amount of the first additional labelled antibody and a first additional unlabelled antibody that is free of any fluorochrome, wherein the first additional labelled antibody and the first additional unlabelled antibody have the same antigen specificity and are specifically reactive to a first additional subpopulation biologic particle in the sample, wherein the first additional labelled antibody, or the first additional labelled antibody and the first additional unlabelled antibody, are present in a quantity sufficient to obtain maximum binding to the first additional subpopulation biologic particle and sufficient to confer upon the first additional subpopulation biologic particle a first additional fluorescence intensity, and wherein the first and second fluorochromes are inducible to fluoresce at different wave lengths.

8. The method for distinguishing at least two subpopulations of biologic particles in a sample as claimed in claim 4, further comprising, between steps (b) and (c), the additional step of selecting a first additional reagent that comprises:

a first amount of a first additional labelled antibody that is labelled solely with a second fluorochrome, or a mixture of the first amount of the first additional labelled antibody and a first additional unlabelled antibody that is free of any fluorochrome, wherein the first additional labelled antibody and the first additional unlabelled antibody have the same antigen specificity and are specifically reactive to a first additional subpopulation biologic particle in the sample, wherein the first additional labelled antibody, or the first additional labelled antibody and the first additional unlabelled antibody, are present in a quantity sufficient to obtain maximum binding to the first additional subpopulation biologic particle and sufficient to confer upon the first additional subpopulation biologic particle a first additional fluorescence intensity, and wherein the first and second fluorochromes are inducible to fluoresce at different wave lengths.

9. The method for distinguishing at least two subpopulations of biologic particles in a sample as claimed in claim 5, further comprising, between steps (b) and (c), the additional step of selecting a second additional reagent that comprises:

a second amount of a second additional labelled antibody that is labelled solely with a second fluorochrome, or a mixture of the first amount of the second additional labelled antibody and a second additional unlabelled antibody that is free of any fluorochrome, wherein the second additional labelled antibody and the second additional unlabelled antibody have the same antigen specificity and are specifically reactive to a second additional subpopulation biologic particle in the sample, wherein the second additional labelled antibody, or the second additional labelled antibody and the second additional unlabelled antibody, are present in a quantity sufficient to obtain maximum binding to the second additional subpopulation biologic particle and sufficient to confer upon the second additional subpopulation biologic particle a second additional fluorescence intensity, and wherein the second amount of the second additional labelled antibody is adjusted, relative to the first amount of the first additional labelled antibody, so that the second additional fluorescence intensity is different from the first additional fluorescence intensity.

10. The method for distinguishing at least two subpopulations of biologic particles in a sample as claimed in claim 6, further comprising, between steps (b) and (c), the additional step of selecting a second additional reagent that comprises:
- a second amount of a second additional labelled antibody that is labelled solely with a second fluorochrome, or
- a mixture of the first amount of the second additional labelled antibody and a second additional unlabelled antibody that is free of any fluorochrome,
- wherein the second additional labelled antibody and the second additional unlabelled antibody have the same antigen specificity and are specifically reactive to a second additional subpopulation biologic particle in the sample,
- wherein the second additional labelled antibody, or the second additional labelled antibody and the second additional unlabelled antibody, are present in a quantity sufficient to obtain maximum binding to the second additional subpopulation biologic particle and sufficient to confer upon the second additional subpopulation biologic particle a second additional fluorescence intensity, and
- wherein the second amount of the second additional labelled antibody is adjusted, relative to the first amount of the first additional labelled antibody, so that the second additional fluorescence intensity is different from the first additional fluorescence intensity.

11. The method for distinguishing at least two subpopulations of biologic particles in a sample as claimed in claim 7, further comprising, between steps (b) and (c), the additional step of selecting a second additional reagent that comprises:
- a second amount of a second additional labelled antibody that is labelled solely with a second fluorochrome, or
- a mixture of the first amount of the second additional labelled antibody and a second additional unlabelled antibody that is free of any fluorochrome,
- wherein the second additional labelled antibody and the second additional unlabelled antibody have the same antigen specificity and are specifically reactive to a second additional subpopulation biologic particle in the sample,
- wherein the second additional labelled antibody, or the second additional labelled antibody and the second additional unlabelled antibody, are present in a quantity sufficient to obtain maximum binding to the second additional subpopulation biologic particle and sufficient to confer upon the second additional subpopulation biologic particle a second additional fluorescence intensity, and
- wherein the second amount of the second additional labelled antibody is adjusted, relative to the first amount of the first additional labelled antibody, so that the second additional fluorescence intensity is different from the first additional fluorescence intensity.

12. The method for distinguishing at least two subpopulations of biologic particles in a sample as claimed in claim 8, further comprising, between steps (b) and (c), the additional step of selecting a second additional reagent that comprises:
- a second amount of a second additional labelled antibody that is labelled solely with a second fluorochrome, or
- a mixture of the first amount of the second additional labelled antibody and a second additional unlabelled antibody that is free of any fluorochrome,
- wherein the second additional labelled antibody and the second additional unlabelled antibody have the same antigen specificity and are specifically reactive to a second additional subpopulation biologic particle in the sample,
- wherein the second additional labelled antibody, or the second additional labelled antibody and the second additional unlabelled antibody, are present in a quantity sufficient to obtain maximum binding to the second additional subpopulation biologic particle and sufficient to confer upon the second additional subpopulation biologic particle a second additional fluorescence intensity, and
- wherein the second amount of the second additional labelled antibody is adjusted, relative to the first amount of the first additional labelled antibody, so that the second additional fluorescence intensity is different from the first additional fluorescence intensity.

13. The method for distinguishing at least two subpopulations of biologic particles in a sample as claimed in claim 10, further comprising, between steps (b) and (c), the additional step of selecting a second additional reagent that comprises:
- a third amount of a third additional labelled antibody that is labelled solely with the second fluorochrome, or
- a mixture of the third amount of the third additional labelled antibody and a third additional unlabelled antibody that is free of any fluorochrome,
- wherein the third additional labelled antibody and the third additional unlabelled antibody have the same antigen specificity and are specifically reactive to a third additional subpopulation biologic particle in the sample,
- wherein the third additional labelled antibody, or the third additional labelled antibody and the third additional unlabelled antibody, are present in a quantity sufficient to obtain maximum binding to the third additional subpopulation biologic particle and sufficient to confer upon the third additional subpopulation biologic particle a third additional fluorescence intensity, and
- wherein the third amount of the third additional labelled antibody is adjusted, relative to the first amount second amounts of additional labelled antibodies, so that the third additional fluorescence intensity is different from the first and second additional fluorescence intensities.

14. The method for distinguishing at least two subpopulations of biologic particles in a sample as claimed in claim 11, further comprising, between steps (b) and (c), the additional step of selecting a second additional reagent that comprises:
- a third amount of a third additional labelled antibody that is labelled solely with the second fluorochrome, or
- a mixture of the third amount of the third additional labelled antibody and a third additional unlabelled antibody that is free of any fluorochrome,
- wherein the third additional labelled antibody and the third additional unlabelled antibody have the same antigen specificity and are specifically reactive to a third additional subpopulation biologic particle in the sample, wherein the third additional labelled antibody, or the third additional labelled antibody and the third additional unlabelled antibody, are present in a quantity sufficient to obtain maximum binding to the third additional subpopulation biologic particle and sufficient to confer upon the third additional subpopulation biologic particle a third additional fluorescence intensity, and wherein the third amount of the third additional labelled antibody is adjusted, relative to the first and second amounts of additional labelled antibodies, so that the third additional fluorescence intensity is different from the first and second additional fluorescence intensities.

15. The method for distinguishing at least two subpopulations of biologic particles in a sample as claimed in claim 12, further comprising, between steps (b) and (c), the additional step of selecting a second additional reagent that comprises:

a third amount of a third additional labelled antibody that is labelled solely with the second fluorochrome, or a mixture of the third amount of the third additional labelled antibody and a third additional unlabelled antibody that is free of any fluorochrome, wherein the third additional labelled antibody and the third additional unlabelled antibody have the same antigen specificity and are specifically reactive to a third additional subpopulation biologic particle in the sample, wherein the third additional labelled antibody, or the third additional labelled antibody and the third additional unlabelled antibody, are present in a quantity sufficient to obtain maximum binding to the third additional subpopulation biologic particle and sufficient to confer upon the third additional subpopulation biologic particle a third additional fluorescence intensity, and wherein the third amount of the third additional labelled antibody is adjusted, relative to the first and second amounts of additional labelled antibodies, so that the third additional fluorescence intensity is different from the first and second additional fluorescence intensities.

16. The method for distinguishing at least two subpopulations of biologic particles in a sample as claimed in claim 14, further comprising, between steps (b) and (c), the additional step of selecting a second additional reagent that comprises:

a fourth amount of a fourth additional labelled antibody that is labelled solely with the second fluorochrome, or a mixture of the fourth amount of the fourth additional labelled antibody and a fourth additional unlabelled antibody that is free of any fluorochrome, wherein the fourth additional labelled antibody and the fourth additional unlabelled antibody have the same antigen specificity and are specifically reactive to a fourth additional subpopulation biologic particle in the sample, wherein the fourth additional labelled antibody, or the fourth additional labelled antibody and the fourth additional unlabelled antibody, are present in a quantity sufficient to obtain maximum binding to the fourth additional subpopulation biologic particle and sufficient to confer upon the fourth additional subpopulation biologic particle a fourth additional fluorescence intensity, and wherein the fourth amount of the fourth additional labelled antibody is adjusted, relative to the first, second, and third amounts of additional labelled antibodies, so that the fourth additional fluorescence intensity is different from the first, second, and third additional fluorescence intensities.

17. The method for distinguishing at least two subpopulations of biologic particles in a sample as claimed in claim 15, further comprising, between steps (b) and (c), the additional step of selecting a second additional reagent that comprises:

a fourth amount of a fourth additional labelled antibody that is labelled solely with the second fluorochrome, or a mixture of the fourth amount of the fourth additional labelled antibody and a fourth additional unlabelled antibody that is free of any fluorochrome, wherein the fourth additional labelled antibody and the fourth additional unlabelled antibody have the same antigen specificity and are specifically reactive to a fourth additional subpopulation biologic particle in the sample, wherein the fourth additional labelled antibody, or the fourth additional labelled antibody and the fourth additional unlabelled antibody, are present in a quantity sufficient to obtain maximum binding to the fourth additional subpopulation biologic particle and sufficient to confer upon the fourth additional subpopulation biologic particle a fourth additional fluorescence intensity, and wherein the fourth amount of the fourth additional labelled antibody is adjusted, relative to the first, second, and third amounts of additional labelled antibodies, so that the fourth additional fluorescence intensity is different from the first, second, and third additional fluorescence intensities.

18. The method for distinguishing at least two subpopulations of biologic particles in a sample as claimed in claim 1, wherein one of said first and second fluorescence intensities is at or near the maximum measurable intensity.

19. The method for distinguishing at least two subpopulations of biologic particles in a sample as claimed in claim 1, wherein the antibody that is labelled with a fluorochrome is selected from the group consisting of an antibody conjugated to the fluorochrome, an antibody attached to a liposome containing the fluorochrome, and an antibody attached to a microsphere containing the fluorochrome.

20. The method for distinguishing at least two subpopulations of biologic particles in a sample as claimed in claim 1, wherein the first fluorochrome is selected from the group consisting of fluorescein, rhodamine, Texas red, a cyanine dye and a phycobiliprotein.

21. The method for distinguishing at least two subpopulations of biologic particles in a sample as claimed in claim 5, wherein said second fluorochrome is selected from the group consisting of fluorescein, rhodamine, Texas red, a cyanine dye and a phycobiliprotein.

22. The method for distinguishing at least two subpopulations of biologic particles in a sample as claimed in claim 1, wherein the particles are cells.

23. The method for distinguishing at least two subpopulations of biologic particles in a sample as claimed in claim 22, wherein the cells are elements of blood.

24. The method for distinguishing at least two subpopulations of biologic particles in a sample as claimed in claim 9, wherein one of said first and second additional fluorescence intensities is at or near the maximum measurable intensity.

25. A diagnostic kit for distinguishing at least two subpopulations of biologic particles in a sample comprising:
- a first reagent that comprises a first labelled antibody that is labelled solely with a first fluorochrome,
- a first diluent that comprises a first unlabelled antibody that is free of any fluorochrome,
- a second reagent that comprises a second labelled antibody that is labelled solely with the first fluorochrome, and
- a second diluent that comprises a second unlabelled antibody that is free of any fluorochrome,
- wherein the first labelled antibody and the first unlabelled antibody have the same antigen specificity and are specifically reactive to a first subpopulation biologic particle in the sample,
- wherein the second labelled antibody and the second unlabelled antibody have the same antigen specificity and are specifically reactive to a second subpopulation biologic particle in the sample, further comprising:
- a first additional reagent that comprises a first additional labelled antibody that is labelled solely with a second fluorochrome, and
- a first additional diluent that comprises a first additional unlabelled antibody that is free of any fluorochrome,
- wherein the first additional labelled antibody and the first additional unlabelled antibody have the same antigen specificity and are specifically reactive to a first additional subpopulation biologic particle in the sample, and
- wherein the first and second fluorochromes are inducible to fluoresce at different wavelengths.

26. The diagnostic kit as claimed in claim 25, further comprising:
- a third reagent that comprises a third labelled antibody that is labelled solely with the first fluorochrome, and
- a third diluent that comprises a third unlabelled antibody that is free of any fluorochrome,
- wherein the third labelled antibody and the third unlabelled antibody have the same antigen specificity and are specifically reactive to a third subpopulation biologic particle in the sample.

27. The diagnostic kit as claimed in claim 26, further comprising:
- a fourth reagent that comprises a fourth labelled antibody that is labelled solely with the first fluorochrome, and
- a fourth diluent that comprises a fourth unlabelled antibody that is free of any fluorochrome,
- wherein the fourth labelled antibody and the fourth unlabelled antibody have the same antigen specificity and are specifically reactive to a fourth subpopulation biologic particle in the sample.

28. The diagnostic kit as claimed in claim 27, further comprising:
- a fifth reagent that comprises a fifth labelled antibody that is labelled solely with the first fluorochrome, and
- a fifth diluent that comprises a fifth unlabelled antibody that is free of any fluorochrome,
- wherein the fifth labelled antibody and the fifth unlabelled antibody have the same antigen specificity and are specifically reactive to a fourth subpopulation biologic particle in the sample.

29. The diagnostic kit as claimed in claim 25, further comprising:
- a second additional reagent that comprises a second additional labelled antibody that is labelled solely with the second fluorochrome, and
- a second additional diluent that comprises a second additional unlabelled antibody that is free of any fluorochrome,
- wherein the second additional labelled antibody and the second additional unlabelled antibody have the same antigen specificity and are specifically reactive to a second additional subpopulation biologic particle in the sample.

30. The diagnostic kit as claimed in claim 26, further comprising:
- a second additional reagent that comprises a second additional labelled antibody that is labelled solely with the second fluorochrome, and
- a second additional diluent that comprises a second additional unlabelled antibody that is free of any fluorochrome,
- wherein the second additional labelled antibody and the second additional unlabelled antibody have the same antigen specificity and are specifically reactive to a second additional subpopulation biologic particle in the sample.

31. The diagnostic kit as claimed in claim 27, further comprising:
- a second additional reagent that comprises a second additional labelled antibody that is labelled solely with the second fluorochrome, and
- a second additional diluent that comprises a second additional unlabelled antibody that is free of any fluorochrome,
- wherein the second additional labelled antibody and the second additional unlabelled antibody have the same antigen specificity and are specifically reactive to a second additional subpopulation biologic particle in the sample.

32. The diagnostic kit as claimed in claim 28, further comprising:
- a second additional reagent that comprises a second additional labelled antibody that is labelled solely with the second fluorochrome, and
- a second additional diluent that comprises a second additional unlabelled antibody that is free of any fluorochrome,
- wherein the second additional labelled antibody and the second additional unlabelled antibody have the same antigen specificity and are specifically reactive to a second additional subpopulation biologic particle in the sample.

33. The diagnostic kit as claimed in claim 30, further comprising:
- a third additional reagent that comprises a third additional labelled antibody that is labelled solely with the second fluorochrome, and
- a third additional diluent that comprises a third additional unlabelled antibody that is free of any fluorochrome,
- wherein the third additional labelled antibody and the third additional unlabelled antibody have the same antigen specificity and are specifically reactive to a third additional subpopulation biologic particle in the sample.

34. The diagnostic kit as claimed in claim 31, further comprising:
   a third additional reagent that comprises a third additional labelled antibody that is labelled solely with the second fluorochrome, and
   a third additional diluent that comprises a third additional unlabelled antibody that is free of any fluorochrome,
   wherein the third additional labelled antibody and the third additional unlabelled antibody have the same antigen specificity and are specifically reactive to a third additional subpopulation biologic particle in the sample.

35. The diagnostic kit as claimed in claim 32, further comprising:
   a third additional reagent that comprises a third additional labelled antibody that is labelled solely with the second fluorochrome, and
   a third additional diluent that comprises a third additional unlabelled antibody that is free of any fluorochrome,
   wherein the third additional labelled antibody and the third additional unlabelled antibody have the same antigen specificity and are specifically reactive to a second additional subpopulation biologic particle in the sample.

36. The diagnostic kit as claimed in claim 34, further comprising:
   a fourth additional reagent that comprises a fourth additional labelled antibody that is labelled solely with the second fluorochrome, and
   a fourth additional diluent that comprises a fourth additional unlabelled antibody that is free of any fluorochrome,
   wherein the fourth additional labelled antibody and the fourth additional unlabelled antibody have the same antigen specificity and are specifically reactive to a fourth additional subpopulation biologic particle in the sample.

37. The diagnostic kit as claimed in claim 35, further comprising:
   a fourth additional reagent that comprises a fourth additional labelled antibody that is labelled solely with the second fluorochrome, and
   a fourth additional diluent that comprises a fourth additional unlabelled antibody that is free of any fluorochrome,
   wherein the fourth additional labelled antibody and the fourth additional unlabelled antibody have the same antigen specificity and are specifically reactive to a fourth additional subpopulation biologic particle in the sample.

38. The diagnostic kit as claimed in claim 25, wherein said particles are cells.

39. A diagnostic kit as claimed in claim 38, wherein said cells are elements of blood.

40. The diagnostic kit as claimed in claim 25, wherein the antibody that is labelled with a fluorochrome is selected from the group consisting of an antibody conjugated to the fluorochrome, an antibody attached to a liposome containing the fluorochrome, and an antibody attached to a microsphere containing the fluorochrome.

41. The diagnostic kit as claimed in claim 25, wherein said first fluorochrome is selected from the group consisting of fluorescein, rhodamine, Texas red, a cyanine dye and a phycobiliprotein.

42. The diagnostic kit as claimed in claim 29, wherein said second fluorochrome is selected from the group consisting of fluorescein, rhodamine, Texas red, a cyanine dye and a phycobiliprotein.

* * * * *